United States Patent
Ungheri et al.

(10) Patent No.: US 6,589,993 B2
(45) Date of Patent: Jul. 8, 2003

(54) TREATING VANCOMYCIN-INTERMEDIATES AND MULTIRESISTANT STAPHYLOCOCCI INFECTION WITH THIAMPHENICOL OR A SALT THEREOF

(75) Inventors: Domenico Ungheri, Parabiago (IT); Luciano Licciardello, Monza (IT)

(73) Assignee: Zambon Group S.p.A., Vicenza (IT)

( * ) Notice: Subject to any disclaimer, the term of this patent is extended or adjusted under 35 U.S.C. 154(b) by 40 days.

(21) Appl. No.: 09/958,945

(22) PCT Filed: Feb. 6, 2001

(86) PCT No.: PCT/EP01/01243

§ 371 (c)(1),
(2), (4) Date: Oct. 16, 2001

(87) PCT Pub. No.: WO01/60344

PCT Pub. Date: Aug. 23, 2001

(65) Prior Publication Data

US 2002/0183246 A1 Dec. 5, 2002

(30) Foreign Application Priority Data

Feb. 16, 2000 (IT) .......................................... MI20A0262

(51) Int. Cl.$^7$ ............................................... A61K 31/16
(52) U.S. Cl. ...................................................... 514/628
(58) Field of Search ......................................... 514/528

(56) References Cited

PUBLICATIONS

M. Ozsan et al: "Antibacterial Susceptibility of *staphylococcus–aureus* isolated from clinical samples" Mikrobiyoloji Bulteni, vol. 23, No. 9, pp. 246–250, 1989.

E. Albini et al: "In vitro antibacterial activity of thiamphenicol gycinate acetylcysteinate against respiratory pathogens" Arzneimittel Forchung, Drug Research, Editio Cantor, vol. 49, No. 6, pp. 533–537.

A Marchese et al.: "In vitro of thianphenicol against methicillin–resistant (MRSA) and vancomycin–intermediat (VISA) *staphylococcus aureus* strains" Abstract of the Interscience Conference on Antimicrobial Agents and 40th Interscience Conference on Antimicrobial Agents and Chemotherapy, vol. 40, pp. 167 2000.

S. Bozza et al.: "In vitro activity of combination thiamphenicol (TAF) and vancomycin (VA) against VA–resistant *E. faecium* (VRE) and methicillin–resistant *S. aureus* (MRSA)"Abstarcts of the Interscience Conference on Antimicrobial Agents and 39$^{th}$ Interscience Conference on Antimicrobial Agents and Chemotherapy, vol. 39. pp. 290 1999.

R. Motomura et al.: "Anti microbial therapy of post operative retroperitoneal space inflammation after radical hysterectomy for carcinoma of the uterus" Current Chemotherapy and Infectuous Disease, vol. 1 and 2; Proceedings of the 11$^{th}$ international Congress and the 19 th Interscience Conference on Antimicrobial agents and chemotherapy.

S.O. Adedeji et al: "Thiamphenicol: use in a developing country. Part I: studies in bacterial sensitivity" West African Journal Of Pharmacology and Drug Research 1974.

B.M. Limson et al: "Thiamphenicol in the treatment of acute respiratory infections." Philippine Journal of Internal Medicine, pp. 145–148 1974.

HC Neu et al: "In–vitro activity of chloramphenicol and thiamphenicol analogs" Antimicrobial Agents and Chemotherapy, vol. 18, No. 2, pp. 311–316 1980.

*Primary Examiner*—Rebecca Cook
(74) *Attorney, Agent, or Firm*—Oblon, Spivak, McClelland, Maier & Neustadt, P.C.

(57) ABSTRACT

The present invention relates to methods of treating vancomycin-intermediates and multiresistant staphylococci infection using thiamphenicol or a salt thereof.

8 Claims, No Drawings

TREATING VANCOMYCIN-INTERMEDIATES AND MULTIRESISTANT STAPHYLOCOCCI INFECTION WITH THIAMPHENICOL OR A SALT THEREOF

This application is a 371 of PCT/EP01/01234 filed Feb. 6, 2001.

The present invention relates to the use of thiamphenicol for the preparation of pharmaceutical compositions useful in the treatment of vancomycin-intermediates and multiresistant Staphylococci infections.

The broad use of antibiotics has significantly increased the number of resistant micro-organisms which are more and more associated to serious pathological states and to mortality among hospitalized patients.

In particular, during the last years, the onset of hospital infections caused by strains of Staphylococci, in particular Staphylococcus aureus, with an intermediate susceptibility, i.e. reduced, to vancomycin (VISA) and other glycopeptides (GISA), has been more and more frequently supported by documentary evidence. These pathogenic strains are generally resistant also to most antibiotics of frequent therapeutical use such as, for example, β-lactames, macrolides, tetracyclines and quinolones.

The characteristics of a significant number of these strains have been widely described by Tenover et al. in Journal of Clinical Microbiology, April 1998, pages 1020–1027. Most of the strains of Staphilococci GISA or GISS studied by Tenover et al. in the above mentioned article, are susceptible to the treatment with trimetoprim-sulphametoxazole association and to the treatment with riphampine while only some strains are susceptible to other antibiotics such as tetracycline, chloramphenicol, gentamicin and ciprofloxacin.

The speed and the frequency of the occurrence of phenomena of reduced susceptibility to those antibiotics up to now proposed for the treatment of infections caused by strains of vancomycin-intermediates and multiresistant Staphylococci, make the identification of other antibiotics effective in this kind of infections, particularly interesting.

Thiamphenicol (The Merck Index, XII ed., No. 9436, page 1587) is a known antibiotic used for the treatment of Gram-positive and Gram-negative bacterial infection. In particular, the activity of thiamphenicol toward many strains of Staphylococci has been supported by documentary evidence in literature [see for example Kayser et al., Postgraduate Medical Journal, 1974, 50(Suppl. 5), 79–83], nevertheless underlining that in vitro thiamphenicol is from 2 to 4 times less active than chloramphenicol.

We have now found that thiamphenicol is particularly effective in the treatment of infections due to strains of Staphylococci vancomycin-intermediates and multiresistant.

It is therefore an object of the present invention, the use of thiamphenicol for the preparation of pharmaceutical composition useful in the treatment of vancomycin-intermediates and multiresistant Staphylococci infections.

Particularly preferred is the use of thiamphenicol for the preparation of a pharmaceutical composition useful for the treatment of vancomycin-intermediates Staphylococci infections. The pharmaceutical compositions useful in the present invention are compositions for enteral or parenteral use containing thiamphenicol or derivatives thereof such as, for example, thiamphenicol glicinate and salts thereof.

The amount of active ingredient, expressed as thiamphenicol, contained in the pharmaceutical composition may change depending on the administration way and to the seriousness of the infection but is generally comprised between 250 mg and 5000 mg per dose, more preferably between 500 mg and 3000 mg.

The pharmaceutical compositions can be in a solid or liquid form, suitable for administering by injectable, oral or aerosol route.

Preferred are the pharmaceutical compositions suitable for administering by injectable route, both endovenous and intramuscular.

Particularly suitable are the pharmaceutical compositions already on the market with the trademark GLITISOL®.

The thiamphenicol efficacy with regard to strains of vancomycin-intermediates (VISA) and multiresistant Staphylococcus aureus has been demonstrated in vitro by calculating the MIC (Minimum Inhibitory Concentration). It is important to underline that the activity of thiamphenicol resulted to be comparable to that as of cloramphenicol well known to be more effective than thiamphenicol against Staphylococci.

With the aim to better illustrate the present invention the following example is now given.

EXAMPLE 1

MIC Determination

The MICs of thiamphenicol and of other antibiotics was obtained by using the method proposed by NCCLS (National Committee for Clinical Laboratory Standards, 1999).

Various antibiotic concentrations were added to bacteria in exponental growth (final inoculum $5 \times 10^5$ ml/cell); dilution in Mb (cation-supplemented Mueller-Hinton broth) and distribution on a microplate by using an automatic diluting machine Biomek 1000 (Beckman, USA). MHb charged with 2% NaCl was used to test the methicillin activity.

The antibiotic concentration which hinders a visible growth after 18–24 hours of incubation at 37° C., was registered as MIC.

S. aureus ATCC 29213 was used as quality control strain.

The obtained results are reported in the following tables.

TABLE 1

MIC of thiamphenicol and of others comparative antibiotics against S. aureus vancomycin-intermediates and multiresistant strains

| Organism (No.) | Antibiotic | MIC (mg/l) Range | 50% | 90% | % susceptible at breakpoint* |
|---|---|---|---|---|---|
| S. aureus (50) Met-R | Thiamphenicol | 4–>64 | 16 | >64 | 66 |
|  | Cloramphenicol | 4–64 | 8 | 64 | 66 |
|  | Vancomicine | 0,5–2 | 1 | 1 | 100 |
|  | Teicoplanin | 0,12–2 | 0,5 | 1 | 100 |
|  | Erythromycin | 64–>64 | >64 | >64 | — |
|  | Clindamycin | 0,06–>64 | >64 | >64 | 8 |
| VISA (2) Met-R | Thiamphenicol | 16 |  |  | 100 |
|  | Cloramphenicol | 8 |  |  | 100 |
|  | Vancomicine | 8 |  |  | — |
|  | Teicoplanin | 8 |  |  | 100 |
|  | Erythromycin | >64 |  |  | — |
|  | Clindamycin | >64 |  |  | — |

Met-R: methicillin resistants
*breakpoints suggested in NCCLS (1999) for Staphylococci, in mg/l: chloramphenicol, ≤8; vancomicine, ≤4; teicoplanin, ≤8; methicillin, ≤8; erythromycin, ≤0.5; clindamycin, ≤0.5.

TABLE 2

MIC (mg/l) of thiamphenicol and other comparative antibiotics

| Strain | Antibiotype | Thia | Clo | Van | Tei | Meth | Ery | Clin |
|---|---|---|---|---|---|---|---|---|
| 1 | Oxa, Cip, Clin, Ery, Gm | 8 | 4 | 0.5 | 0.25 | >64 | >64 | >64 |
| 2 | Oxa, Clin, Ery, Fos | >64 | 64 | 1 | 0.5 | >64 | >64 | >64 |
| 3 | Oxa, Cip, Clin, Ery, Gm | 16 | 4 | 1 | 1 | >64 | >64 | >64 |
| 4 | Oxa, Cip, Ery, Gm | 8 | 4 | 1 | 0.5 | >64 | >64 | ≦0.06 |
| 5 | Oxa, Cip, Clin, Ery | >64 | 64 | 1 | 1 | >64 | >64 | >64 |
| 6 | Oxa, Clin, Ery, Gm | >64 | 64 | 1 | 1 | >64 | >64 | >64 |
| 7 | Oxa, Cip, Ery, Gm | 16 | 8 | 0.5 | 0.25 | 32 | >64 | ≦0.06 |
| 8 | Oxa, Cip, Clin, Ery | >64 | 64 | 1 | 0.25 | >64 | >64 | >64 |
| 9 | Oxa, Cip, Clin, Ery, Gm | 8 | 8 | 1 | 0.25 | >64 | >64 | >64 |
| 10 | Oxa, Cip, Clin, Ery, Gm | 4 | 4 | 1 | 0.25 | >64 | >64 | 64 |
| 11 | Oxa, Clin, Ery, Rif | >64 | 64 | 1 | 1 | >64 | >64 | >64 |
| 12 | Oxa, Cip, Clin, Ery | >64 | 64 | 1 | 1 | >64 | >64 | >64 |
| 13 | Oxa, Cip, Clin, Ery | 16 | 8 | 1 | 1 | >64 | >64 | >64 |
| 14 | Oxa, Clin, Cip, Ery | 16 | 8 | 1 | 0.5 | >64 | >64 | >64 |
| 15 | Oxa, Cip, Clin, Ery, Gm | 16 | 8 | 0.5 | 0.25 | >64 | >64 | >64 |
| 16 | Oxa, Cip, Clin, Ery | 8 | 8 | 1 | 1 | >64 | >64 | >64 |
| 17 | Oxa, Cip, Clin, Ery | 16 | 8 | 0.5 | 0.25 | 64 | >64 | >64 |
| 18 | Oxa, Cip, Clin, Ery, Gm | >64 | 64 | 1 | 1 | >64 | >64 | >64 |
| 19 | Oxa, Cip, Clin, Ery, Gm | 16 | 8 | 1 | 1 | >64 | >64 | >64 |
| 20 | Oxa, Cip, Clin, Ery, Gm | >64 | 64 | 1 | 0.25 | >64 | >64 | 64 |
| 21 | Oxa, Cip, Clin, Ery, Gm | >64 | 64 | 1 | 0.5 | >64 | >64 | >64 |
| 22 | Oxa, Cip, Clin, Ery | 16 | 8 | 0.5 | 0.25 | >64 | >64 | >64 |
| 23 | Oxa, Cip, Clin, Ery, Gm | >64 | 64 | 1 | 0.5 | >64 | >64 | >64 |
| 24 | Oxa, Cip, Clin, Ery, Gm | >64 | 64 | 1 | 0.5 | >64 | >64 | >64 |
| 25 | Oxa, Cip, Clin, Ery, Gm | 16 | 8 | 1 | 1 | >64 | >64 | 64 |
| 26 | Oxa, Cip, Clin, Ery, Fos, Gm | 16 | 8 | 1 | 1 | >64 | >64 | 64 |
| 27 | Oxa, Cip, Clin, Ery, Fos, Gm | 16 | 8 | 1 | 1 | >64 | >64 | 64 |
| 28 | Oxa, Cip, Clin, Ery, Gm | >64 | 64 | 1 | 0.5 | >64 | >64 | >64 |
| 29 | Oxa, Clin, Ery, Fos | 16 | 8 | 1 | 0.5 | >64 | >64 | >64 |
| 30 | Oxa, Cip, Clin, Ery, Gm, SXT, Dox | 16 | 8 | 0.5 | 1 | 64 | >64 | 16 |
| 31 | Oxa, Cip, Clin, Fox, Ery, Gm | 16 | 8 | 1 | 0.5 | >64 | >64 | >64 |
| 32 | Oxa, Cip, Clin, Ery, Gm, SXT, Rif | >64 | 64 | 1 | 0.5 | >64 | >64 | 64 |
| 33 | Oxa, Cip, Clin, Ery, Gm | >64 | 64 | 0.5 | 0.5 | >64 | >64 | >64 |
| 34 | Oxa, Cip, Clin, Ery, Gm | >64 | 64 | 0.5 | 0.25 | >64 | >64 | >64 |
| 35 | Oxa, Cip, Clin, Ery, Gm | 16 | 8 | 1 | 0.5 | >64 | >64 | 64 |
| 36 | Oxa, Cip, Clin, Ery, Fos | 16 | 8 | 0.5 | 1 | >64 | >64 | 64 |
| 37 | Oxa, Cip, Clin, Ery, Fos, Gm | 16 | 8 | 0.5 | 0.25 | 64 | 64 | 64 |
| 38 | Oxa, Cip, Ery, Gm | 8 | 8 | 0.5 | 0.25 | >64 | >64 | ≦0.06 |
| 39 | Oxa, Cip, Clin, Ery, Fos, Gm | 16 | 8 | 0.5 | 0.25 | 64 | 64 | 64 |
| 40 | Oxa, Cip, Clin, Ery, Gm | 16 | 8 | 0.5 | 0.25 | >64 | >64 | >64 |
| 41 | Oxa, Cip, Clin, Ery | 16 | 8 | 0.5 | 0.25 | >64 | >64 | 64 |
| 42 | Oxa, Cip, Clin, Ery, Gm | 8 | 8 | 0.5 | 0.12 | >64 | >64 | 64 |
| 43 | Oxa, Cip, Clin, Ery, Gm | 16 | 8 | 0.5 | 0.5 | >64 | >64 | 64 |
| 44 | Oxa, Cip, Clin, Ery, Gm, Rif, Dox | 16 | 8 | 1 | 1 | 64 | >64 | 64 |
| 45 | Oxa, Cip, Clin, Ery, Gm, Rif, Dox, Fos | 16 | 8 | 1 | 0.5 | >64 | >64 | 64 |
| 46 | Oxa, Clin, Ery, Fos | 16 | 8 | 0.5 | 0.25 | >64 | >64 | 64 |
| 47 | Oxa, Cip, Clin, Ery, Gm | 8 | 8 | 0.5 | 0.12 | >64 | >64 | 64 |
| 48 | Oxa, Cip, Clin, Ery | >64 | 64 | 2 | 2 | 64 | >64 | 64 |
| 49 | Oxa, Cip, Ery, Gm | 16 | 8 | 1 | 0.5 | >64 | >64 | ≦0.06 |
| 50 | Oxa, Cip, Clin, Ery, Gm, Rif, Dox | >64 | 64 | 1 | 0.5 | >64 | >64 | >64 |
| 51 VISA | Oxa, Cip, Clin, Ery | 16 | 8 | 8 | 8 | >64 | >64 | >64 |
| 52 VISA | Oxa, Cip, Clin, Ery | 16 | 8 | 8 | 8 | >64 | >64 | >64 |

Thia: thiamphenicol;
Clo: cloramphenicol;
Van: vancomycine,
Tei: teicoplanine;
Met: methicilline;
Ery: erythromycin;
Clin: clindamycin;
Oxa: oxacillin;
Cip: ciprofloxacin;
Fos: fosfomycin;
Gm: gentamicin;
Rif: rifampicin;
SXT: co-trimoxazole;
Dox: doxycycline.

What is claimed is:

1. A method of treating vancomycin-intermediates and multiresistant Staphylococci infection in a patient infected with vancomycin-intermediates and multiresistant Staphylococci bacteria comprising administering thiamphenicol or a salt thereof to said patient in an amount effective to treat said infection.

2. The method of claim 1, wherein said thiamphenicol is thiamphenicol glicinate or a salt thereof.

3. The method of claim 1, wherein said administering comprises injecting said thiamphenicol into said patient.

4. The method of claim 3, wherein said administering comprises endovenous injecting.

5. The method of claim 3, wherein said administering comprises intramuscular injecting.

6. The method of claim 1, wherein said thiamphenicol is administered in an amount from 250 mg to 5000 mg.

7. The method of claim 1, wherein said thiamphenicol is administered in an amount from 500 mg to 3000 mg.

8. The method of claim 1, wherein said administering comprises oral administration.

* * * * *